United States Patent [19]

Smith et al.

[11] Patent Number: 4,528,407

[45] Date of Patent: Jul. 9, 1985

[54] CATALYTIC PROCESS FOR PREPARATION OF ORTHO-ALKYLATED PHENOLS

[75] Inventors: William E. Smith, Schenectady; Richard A. Battista, Albany, both of N.Y.

[73] Assignee: General Electric Company, Pittsfield, Mass.

[21] Appl. No.: 314,622

[22] Filed: Oct. 26, 1981

Related U.S. Application Data

[63] Continuation-in-part of Ser. No. 163,486, Jun. 27, 1980, abandoned.

[51] Int. Cl.$^3$ .................. C07C 37/16; C07C 39/06
[52] U.S. Cl. .................................. 568/804; 568/789; 568/794; 502/324; 502/328
[58] Field of Search ............... 568/804, 744, 794, 789; 502/324, 328

[56] References Cited

U.S. PATENT DOCUMENTS

| 3,306,875 | 2/1967 | Haye | 568/730 |
|---|---|---|---|
| 3,843,606 | 10/1974 | Van Sorge | 568/804 |
| 3,873,628 | 3/1975 | Van Sorge | 568/804 |
| 3,962,126 | 6/1976 | Pecak | 568/804 |
| 3,971,832 | 7/1976 | Watanabe et al. | 568/804 |
| 3,972,836 | 8/1976 | Van Sorge | 568/804 |
| 4,041,085 | 8/1977 | Frabetti | 568/804 |

FOREIGN PATENT DOCUMENTS 2127083 12/1971 Fed. Rep. of Germany ...... 568/804

*Primary Examiner*—Werren B. Lone
*Attorney, Agent, or Firm*—Hedman, Gibson, Costigan & Hoare

[57] ABSTRACT

An improved catalytic process for selectively ortho-alkylating a phenolic compound which comprises reacting a phenolic compound with an alcohol, optionally in the presence of water, and a catalyst composite consisting essentially of the calcination residue obtained from heating an admixture of magnesium carbonate and/or magnesium hydroxide and a manganese compound.

17 Claims, No Drawings

CATALYTIC PROCESS FOR PREPARATION OF ORTHO-ALKYLATED PHENOLS

BACKGROUND OF THE INVENTION

This application is a continuation-in-part of copending application Ser. No. 163,486, filed June 27, 1980 now abandoned. This invention relates to an improved catalytic process for the preparation of ortho-alkylated phenols which comprises reacting a phenolic compound with an alcohol, optionally in the presence of water, and a catalyst composite consisting essentially of the calcination residue obtained from an admixture of magnesium carbonate and/or magnesium hydroxide and a manganese compound.

DESCRIPTION OF THE PRIOR ART

Van Sorge in U.S. Pat. No. 3,843,606—issued Oct. 22, 1974, describes the preparation of ortho-alkylated phenols using a porous magnesium oxide powder catalyst bonded with an inert organic cellulose polymeric binder, e.g. the magnesium oxide catalyzed alkylation of phenols with methanol to form ortho-cresol, 2,6-xylenol, and 2,4,6-mesitol at temperatures of at least 460° C. without reduction in catalytic activity for periods in excess of 500 hours.

Pecak in U.S. Pat. No. 3,962,126—issued June 8, 1976 describes the reactivation of a carbonized magnesium oxide-manganese oxide alkylation catalyst by contacting a deactivated catalyst with oxygen and water at a temperature below 300° C. to restore ortho-alkylation catalyst activity.

Van Sorge in U.S. Pat. No. 3,972,836—issued Aug. 3, 1976 describes the ortho-alkylation of phenols employing catalysts derived from the calcination of blends of magnesium oxide powder and manganese oxide powders. The improved catalytic alkylation process is described as effective at temperatures as low as 420° C. preferably employed at 460° to 500° C. Effective catalyst activity is reported as being in excess of 1,000 hours.

Van Sorge in U.S. Pat. No. 3,974,229, issued Aug. 10, 1976 describes the ortho-alkylation of phenols employing catalysts comprising magnesium oxide powers mixed with manganese oxides.

Van Sorge in U.S. Pat. No. 3,873,628, issued Mar. 25, 1975, describes the ortho-alkylation of phenols employing magnesium oxide-manganese sulfate catalysts.

Frabetti in U.S. Pat. No. 4,041,085 describes a process for ortho-alkylation of phenols employing magnesium oxide catalysts with an inert binder in the presence of water vapor.

Unexpectedly the improved catalytic process of this invention permits ortho-alkylation of phenols continuously for 1500–1800 hours at moderate temperatures at high selectivity and high conversion efficiencies when compared to the catalytic processes of the prior art.

DESCRIPTION OF THE INVENTION

This invention embodies an improved catalytic process for the preparation of ortho-alkylated phenols which comprises reacting a phenolic compound with an alcohol, optionally in the presence of water, in the presence of a catalyst consisting essentially of the calcination residue derived from heating an admixture of magnesium carbonate and/or magnesium hydroxide and a manganese compound.

The present invention describes a catalytic ortho-alkylation process which comprises reacting a phenolic compound of the formula:

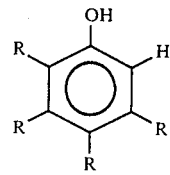

where each R is a monovalent substituent selected from the group consisting of hydrogen, alkyl, phenyl, and alkyl-substituted phenyl with an alcohol selected from the group consisting of $C_{1-6}$ alkyl alcohols at a temperature from about 300° C. to about 500° C. in the presence of a catalyst composite consisting essentially of a calcination residue derived at said reaction temperatures from an admixture of magnesium carbonate and/or magnesium hydroxide and a manganese compound.

The phenolic compounds are well-known and include any of the phenolics described by Van Sorge in U.S. Pat. No. 3,972,836 whose descriptions are incorporated herein by reference. Illustratively, phenolics include phenol itself, i.e. hydroxy benzene, ortho-cresol, ortho-phenyl phenol, ortho-ethyl phenol, and phenols in which there are alkyl or aryl groups in the meta- and para-positions. The phenolic compounds can be represented by the formula:

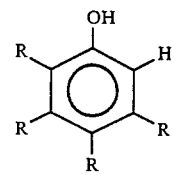

where each R is a monovalent substituent selected from the group consisting of hydrogen, alkyl, e.g., $C_1$–$C_{12}$ alkyl, phenyl and alkyl-substituted phenyl, e.g., $C_1$–$C_{12}$ alkyl-substituted phenyl.

The alcohols are also well-known and include any of those described by Van Sorge and include alkyl alcohols, e.g. saturated aliphatic alcohols, such as methyl, ethyl, propyl, isopropyl, butyl, isobutyl, tert-butyl, amyl, isoamyl, hexyl, heptyl, octyl, nonyl, decyl, undecyl, lauryl, cetyl, cyclohexyl, and the like, alcohols. Especially preferred are alcohols containing up to 6 carbon atoms. Most preferred is methanol.

The pressures used in carrying out the instant reaction can be varied widely and are not critical. Depending upon the temperatures used, the ratio and kind of ingredients, the apparatus, etc., either atmospheric, superatmospheric and even subatmospheric pressures can be employed. As is well known, increases of pressure during the alkylation reaction usually accelerate the rate of reaction. Although the examples in the instant application are carried out at atmospheric pressures, this was in part due to the simplicity of the apparatus. It is contemplated that in large scale commercial production with more sophisticated equipment to effect certain results, such as rate of reaction, yield, purity, etc., superatmospheric pressures, ranging from atmospheric pressure to as high as 60–100 psig or higher may be employed without departing from the scope of the invention.

The pre-calcined catalyst composite admixture can be formed by the combination of magnesium carbonate and/or magnesium hydroxide and manganese hydroxide with subsequent calcination at elevated temperatures to form the active catalyst composite.

The preparation of a magnesium carbonate and magnesium hydroxide and manganese hydroxide blend is conveniently carried out by precipitating manganese hydroxide in the presence of basic magnesium carbonate, i.e. $xMgCO_3.Mg(OH)_2.xH_2O$—where independently each x is a number average of from about 3 to about 5, from a water soluble salt of manganese in the presence of a base.

The resulting admixture $xMgCO_3.xH_2O$ and $Mn(OH)_2$ in water-paste form can be shaped into conventional catalyst pellets by extrusion, molding, or other shaping techniques using state of the art commercial pelletizers. The resulting admixture in pellet form can be charged to the alkylation catalyst bed with subsequent calcination at elevated temperatures generally of from 300° C. to 500° C. or higher.

Reaction temperature can range from about 300° C. to a temperature at which deleterious decomposition of the reactants catalysts or products occurs.

Water-soluble synthetic resins such as, polyvinyl alcohol polymers, acrylics, sodium carboxymethylcellulose, and methylcellulose can be used as shaping aids in the wetpelleting of the magnesium-manganese catalyst composites. Polyphenylene oxides can also be used as shaping aids.

Examples of polyphenylene oxides that can be used in the process of the present invention are described by Hay in U.S. Pat. No. 3,306,875 which is herein incorporated by reference. A preferred polyphenylene oxide is poly-(2,6-dimethyl-1,4-phenylene)oxide. Hereinafter polyphenylene oxide refers to poly-(2,6-dimethyl-1,4-phenylene)oxide.

In a presently preferred embodiment a "basic" magnesium carbonate-manganese hydroxide admixture is heated to substantially evaporate all water entrained in $Mn(OH)_2$ co-precipitated in combination with "basic" $MgCO_3$. In a still further preferred embodiment the resulting dried admixture is reduced in particle size, combined with particulate polyphenylene oxide, and compression molded in conventional catalyst-tableting equipment to form catalyst pellets having enhanced physical properties when used in the process of this invention.

Although the catalyst composite has been described heretofore with reference to "basic" magnesium carbonate, catalyst compositions providing improved activity are also obtained where $Mn(OH)_2$ is co-precipitated in an aqueous slurry containing either only $MgCO_3$ or only $Mg(OH)_2$. The resulting $MgCO_3$ containing co-precipitated $Mn(OH)_2$ per se, or $Mg(OH)_2$ containing co-precipitated $Mn(OH)_2$ per se, may be combined or used separately as improved alkylation catalysts in the process of this invention.

Summarily, any combination of $MgCO_3$ per se, and/or $Mg(OH)_2$ per se, as well as "basic" $MgCO_3$ containing co-precipitated $Mn(OH)_2$ can be combined in an aqueous solution, optionally with aqueous wetting agents, with subsequent drying to remove entrained water, and further optionally combined with a polyphenylene oxide resin, to provide improved catalyst composites in the ortho-alkylation of phenolic compounds.

The catalyst composites of this invention using wet- or dry-pelleting procedures—as charged to the alkylation reactor—contain magnesium in a form consisting essentially of $MgCO_3$ and/or $Mg(OH)_2$ in combination with $Mn(OH)_2$ as opposed to and in contradistinction to all of the prior art which describes the use of MgO alone or in combination with $Mn(OH)_2$ and binders.

In the present invention the active form of the catalyst is formed when magnesium carbonate and/or magnesium hydroxide-manganese compound mixture is calcined or heated and decomposes to produce the magnesium oxide-manganese oxide composite catalyst in a form which is substantially more active, with respect to the present alkylation reaction than the catalysts of the prior art. The increased activity of the catalyst allows the reaction to be conducted at lower temperatures and/or higher reactant space velocities. The process provides a higher percent conversion to ortho-alkylated products even at higher throughput and lower temperatures than catalysts of the prior art. The present invention also exhibits lifetimes much improved over those of the prior art catalysts. Catalyst lifetimes as long as 2200 hours have been observed using the process of the present invention.

Water can be included in the reactant vapor stream preferably in concentrations of about 10% to about 30% by weight of the reactants to suppress the formation and build-up of carbonaceous non-volatile species, or coke, which can become significant especially at lower reactor temperatures.

In any alkylation process a portion of the alcohol fed as a reactant is decomposed to synthesis gas e.g. $CO, H_2$, etc. which are usually burned. The present process also results in a reduction in the decomposition of the alcohol feed to synthesis gas over the prior art. A typical prior art process results in approximately 35 percent of the methanol feed being lost to decomposition. The process of the present invention due to lower reaction temperatures and other factors results in only approximately 15 percent of the methanol being decomposed.

GENERAL ORTHO-ALKYLATION PROCESS PROCEDURE

The following general procedure was used to evaluate the prior art catalysts and the catalysts of the invention described herein. A series of 2,6-xylenol alkylations were carried out contrasting the invention catalysts with commercially available prior art catalyst composites reportedly containing, on a weight percent basis, typically, 65% MgO:31% $Mg(OH)_2$:4% $Mn_2O_3$. The prior art catalysts formed into 3/16" dia.×3/16" long cylindrical pellets, reportedly, after pelletizing had been heated for 6 hrs. at 370° C. Where the expression "commercial catalyst" appears in the following examples the above-referenced catalyst composite was the catalyst charged to the alkylation reactor under the reaction conditions described.

Phenolic feedstocks including water were pumped from a reservoir through a ¼" stainless steel tube into a vertical vaporizer, i.e. a 12" long stainless steel tube having a 0.8" I.D. and a 1" O.D. The vaporizer was partially immersed in a bath of fused salt to a depth of about 6". Vaporized feedstock was fed into a 24" long stainless steel tube reactor having a 0.8" I.D. through a 1" length of ½" I.D. stainless steel pipe located 5½ above the bottom of the vaporizer and attached to the reactor 13" above the bottom of the reactor. The reactor was immersed in a fused salt bath to a depth of about 14".

The reaction temperature, estimated as the equivalent of the salt bath temperature was measured throughout each alkylation reaction. The catalyst bed was filled to a constant volume of 110 milliliters with pelletized catalyst which filled the reactor tube to a depth of 12″. Feedstock and water vapors were fed into the top of the catalyst bed and reaction product vapors left the bottom of the reactor through a ⅜″ I.D. stainless steel tube. The product vapors were passed to a water-cooled condenser-receiver, and the condensed vapors containing any unreacted feedstock as well as the desired end-product 2,6-xylenol were analyzed by VPC techniques. Non-condensed gases containing hydrogen, carbon monoxide, carbon dioxide, methane and ethane were scrubbed and passed through a wet-test meter to determine their volume.

A resume of the process parameters and results associated with the ortho-alkylation process of this invention employing the catalysts of this invention contrasted with prior art catalysts is set out in the Tables hereafter. The best mode of preparing various catalysts within the scope of this invention is also set out in the examples.

EXAMPLE 1

Catalyst Preparation

A slurry of 518.9 grams of "basic" $MgCO_3$ in 2000 ml. of distilled water was combined with 40.0 grams of $Mn(NO_3)_2$, diluted to 500 ml. with distilled water over approximately a 4-minute time period. 10.8 grams of a 50% caustic NaOH solution diluted to 500 ml. with distilled water was added to the resulting admixture over approximately 4 minutes, followed by stirring for one hour at room temperature. The slurry was vacuum filtered, washed with 1500 ml. of distilled water, resuspended by homogenizing in water and vacuum filtered again. The "resuspension" procedure was repeated four times for a total of five resuspensions and five vacuum filtrations. The filtrate was dried overnight under vacuum in a 103° C. oven and ground to a fine powder. The powder was blended with sufficient polyphenylene oxide to provide 90 parts by weight of "basic" $MgCO_3$ co-precipitated with $Mn(OH)_2$ and 10 parts by weight of polyphenylene oxide. The 90:10 powder blend was precompressed in a tableting press, ground and sifted through a #25 screen, and tableted to form 3/16″×⅛″ pellets.

Catalyst and Process Testing

The reactor—after charging with catalyst pellets—was capped and immersed in a salt bath at 370° C. The catalyst was pre-heated while nitrogen was passed through the bath-heated catalyst bed at a volumetric rate corresponding to 2 SCFH (standard cubic feet per hour) for 15 minutes.

Immediately following the 15-minute period under continuous process reaction conditions, liquid feedstock which contained methanol, phenol, ortho-cresol and water, was continuously fed to the reactor at a rate of 228 ml/hour throughout a 286-hour test. The resulting feed vapors were continuously passed through the catalyst as described above. The conditions and results of the test are set forth in Table 1.

TABLE 1

| Feed Composition | | |
|---|---|---|
| Molar Ratio Methanol to Phenolic Compounds | 4:1 | |
| Molar Ratio Phenol to Ortho-Cresol | 60:40 | |
| Wt. % Water in Feed | 23 | |
| Operating Conditions | | |
| Temperature (°C.) | | 445–460 |
| LHSV (hr.$^{-1}$)[1] | | 2.07 |
| Pressure (psig) | | 0 |
| Phenolic Distribution (wt. %) | 189 HR[2] | 286 HR[3] |
| o-cresol | 27.38 | 25.19 |
| 2,6-xylenol | 65.80 | 67.83 |
| 2,4,6-mesitol | 3.14 | 3.22 |
| Phenol | 3.26 | 3.40 |
| Off Gas | 0.455 | 0.580 |

[1]LHSV is the liquid hourly space velocity and defines the volume of liquid per volume of catalyst per hour.
[2]Temperature at the indicated elapsed time was 455° C.
[3]Temperature at the indicated elapsed time was 460° C.

EXAMPLE II

Catalyst Preparation

A slurry of 518.9 grams of "basic" $MgCO_3$ in 2000 ml. of distilled water was combined with 40.0 grams of $Mn(NO_3)_2$, diluted to 500 ml. with distilled water over approximately a 4-minute time period. 10.8 grams of a 50% caustic NaOH solution diluted to 500 ml. with distilled water was added to the resulting admixture over approximately 4 minutes, followed by stirring for one hour at room temperature. The slurry was vacuum filtered, washed with 1500 ml. of distilled water, resuspended by homogenizing in water and vacuum filtered again. The "resuspension" procedure was repeated four more times. The final "resuspension" was carried out in 1250 ml. of acetone. The filtrate was dried overnight under vacuum in a 120° C. oven and ground to a fine powder. The powder was blended with sufficient polyphenylene oxide to provide 80 parts by weight of "basic" $MgCO_3$ co-precipitated with $Mn(OH)_2$ and 20 parts by weight of polyphenylene oxide. The 80:20 blend was tabletted to 1/16″×3/16″ catalyst pellets in a tableting press.

Catalyst and Process Testing

The reactor—after charging with catalyst pellets—was capped and immersed in the salt bath at 370° C. The catalyst was pre-heated while nitrogen was passed through the bath-heated catalyst bed at a volumetric rate corresponding to 2 SCFH (standard cubic feet per hour) for 15 minutes.

Immediately following the 15-minute period, under continuous process reaction conditions, liquid feedstock which contained methanol, phenol, ortho-cresol and water, was continuously fed to the reactor at a rate of 228 ml/hour throughout a 311-hour test. The resulting feed vapors were continuously passed through the catalyst as described above. The conditions and results of the test are set forth in Table II.

TABLE II

| Feed Composition | | |
|---|---|---|
| Molar Ratio Methanol to Phenolic Compounds | 4:1 | |
| Molar Ratio Phenol to Ortho-Cresol | 60:40 | |
| Wt. % Water in Feed | 23 | |
| Operating Conditions | | |
| Temperature (°C.) | | 440–453 |
| LHSV (hr.$^{-1}$)[1] | | 2.07 |
| Pressure (psig) | | 0 |
| Phenolic Distribution (wt. %) | 195 HR[2] | 311 HR[3] |
| o-cresol | 21.14 | 16.94 |
| 2,6-xylenol | 71.28 | 75.72 |
| 2,4,6-mesitol | 4.05 | 3.83 |
| Phenol | 3.54 | 3.51 |

TABLE II-continued

| | | |
|---|---|---|
| Off Gas | 0.470 | 0.520 |

[1]LHSV is the liquid hourly space velocity and defines the volume of liquid per volume of catalyst per hour.
[2]Temperature at the indicated elapsed time was 453° C.
[3]Temperature at the indicated elapsed time was 453° C.

COMPARATIVE PRIOR ART CATALYST PROCESS DATA

Prior art commercial catalyst composites containing, on a weight percent basis, typically, 65% MgO:31% Mg(OH)$_2$:4% Mn$_2$O$_3$ which had been formed into 3/16" dia.×3/16" long cylindrical pellets, and which after pelletizing had been heated for 6 hrs., at 370° C., were charged to a reactor as described in the General Ortho-Alkylation Process Procedure above. The reactor was capped and immersed in a salt bath at 370° C. The catalyst was pre-heated by passing nitrogen through the bath-heated commercial catalyst bed at a volumetric rate corresponding to 2 SCFH (standard cubic feet per hour) for 15 minutes.

Immediately following the 15-minute catalyst preheat, under continuous process reaction conditions, liquid feedstock which contained methanol, phenol, ortho-cresol and water, was continuously fed at a rate of 190 ml/hour throughout a 456-hour test. The resulting feed vapors were continuously passed through the catalyst as described above. The conditions and results of the test are set forth in Table III.

TABLE III

| Feed Composition | | |
|---|---|---|
| Molar Ratio Methanol to Phenolic Compounds | 4:1 | |
| Molar Ratio Phenol to Ortho-Cresol | 60:40 | |
| Wt. Water in Feed | 3 | |
| Operating Conditions | | |
| Temperature (°C.) | 470–485 | |
| LHSV (hr.$^{-1}$)[1] | 1.72 | |
| Pressure (psig) | 0 | |
| Phenolic Distribution (wt. %) | 200 HR[2] | 456 HR[3] |
| o-cresol | 31.99 | 45.85 |
| 2,6-xylenol | 60.30 | 34.95 |
| 2,4,6-mesitol | 2.04 | 0.69 |
| Phenol | 5.33 | 18.18 |
| Off Gas | 0.710 | 0.530 |

[1]LHSV is the liquid hourly space velocity and defines the volume of liquid per volume of catalyst per hour.
[2]Temperature at the indicated elapsed time was 487° C.
[3]Temperature at the indicated elapsed time was 500° C.

In preferred embodiments of this invention, set out in Examples IV and V which follow, respectively, a catalyst preparation employs a catalyst "resuspension" carried out in the presence of methylene chloride and a catalyst preparation which employs the incorporation of a manganese moiety in combination with "basic" magnesium carbonate carried out at temperatures of at least 100° F. or higher. These embodiments are the subject matter of W. E. Smith's, Ser. No. 182,679, filed Aug. 29, 1980 and Battista, Bennett and Kokoszka Ser. No. 162,358, filed June 24, 1980, respectively, filed contemporaneously herewith which have been found to provide improved results in the practice of this invention. These improvements are also disclosed herein although not essential to the utility of this invention.

EXAMPLE IV

Catalyst Preparation

A slurry of 453.2 grams of "basic" MgCO$_3$ in 2000 ml. of distilled water was combined with 40.0 grams of Mn(NO$_3$)$_2$, diluted to 500 ml. with distilled water over approximately a 4-minute time period. 10.8 grams of a 50% caustic NaOH solution diluted to 500 ml. with distilled water was added to the resulting admixture over approximately 4 minutes, followed by stirring for one hour at room temperature. The slurry was vacuum filtered, washed with 1500 ml. of distilled water, resuspended by homogenizing in water and vacuum filtered again. The "resuspension" procedure was repeated four more times. The final "resuspension" was carried out in 1250 ml. of acetone. The filtrate was dried overnight under vacuum in a 120° C. oven and ground to a fine powder. The powder was blended with sufficient polyphenylene oxide to provide 80 parts by weight of "basic" MgCO$_3$ co-precipitated with Mn(OH)$_2$ and 20 parts by weight of polyphenylene oxide. 600 ml. of methylene chloride was added to the 80:20 blend to form a uniformly moist paste. The paste was dried overnight under vacuum in a 50° C. oven. The dried powder was ground to a fine powder, tabletted to 1/16"×3/16" tablets in a tableting press.

Catalyst and Process Testing

The reactor—after charging with catalyst pellets—was capped and immersed in the salt bath at 370° C. The catalyst was pre-heated by passing nitrogen through the bath-heated catalyst bed at a volumetric rate corresponding to 2 SCFH (standard cubic feet per hour) for 15 minutes.

Immediately following, under continuous process reaction conditions, liquid feedstock which contained methanol, phenol, ortho-cresol and water, was continuously fed at a rate of 228 ml/hour throughout a 504-hour test. The resulting feed vapors were continuously passed through the catalyst as described above. The conditions and results of the test are set forth in Table IV.

TABLE IV

| Feed Composition | | | |
|---|---|---|---|
| Molar Ratio Methanol to Phenolic Compounds | 4:1 | | |
| Molar Ratio Phenol to Ortho-Cresol | 60:40 | | |
| Wt. % Water in Feed | 23 | | |
| Operating Conditions | | | |
| Temperature (°C.) | 455–455 | | |
| LHSV (hr.$^{-1}$)[1] | 2.07 | | |
| Pressure (psig) | 0 | | |
| Phenolic Distribution (wt. %) | 198 HR[2] | 504 HR[3] | TWA[4] |
| o-cresol | 15.16 | 28.86 | 23.67 |
| 2,6-xylenol | 78.98 | 66.54 | 69.54 |
| 2,4,6-mesitol | 3.89 | 3.02 | 3.90 |
| Phenol | 1.27 | 3.33 | 2.95 |
| Off Gas | 0.490 | 0.335 | 0.337 |

[1]LHSV is the liquid hourly space velocity and defines the volume of liquid per volume of catalyst per hour.
[2]Temperature at the indicated elapsed time was 455° C.
[3]Temperature at the indicated elapsed time was 455° C.
[4]Time-weighted average of numerous values obtained, at generally uniform intervals throughout the 504-hour test.

EXAMPLE V

Catalyst Preparation

Distilled water (2000 ml) was added to a 5000 ml round-bottom glass flask equipped with a thermometer, a stirrer, and a variac-controlled heating mantle. The water was heated to a temperature of 82° C. and 518.9 grams of "basic" magnesium carbonate, i.e. 5 MgCO$_3$.Mg(OH)$_2$.5H$_2$O (BMC), was added to the heated water with stirring to form a slurry with substantially all the added BMC suspended therein. Stirring was continued and a nitrogen purge was initiated. A dilute dropwise addition of aqueous solution of manganous nitrate $Mn(NO_3)_2$ to the slurry was begun. (The $Mn(NO_3)_2$ solution was prepared by diluting 40.0 grams of a 50% aqueous solution of the manganous nitrate by adding, with stirring, sufficient distilled water to form a 450 ml solution.) The slow addition of the entire dilute manganous nitrate solution was completed in 4 minutes, 11 seconds.

The resulting reaction mixture or slurry containing the dilute manganous nitrate solution with BMC suspended therein was stirred for 6 hours at 82° C. in a closed atmosphere with nitrogen blanketing the reaction mixture. The resulting suspension of BMC with manganous hydroxide precipitated or deposited thereon was separated from the balance of the reaction mixture by filtration using a coarse fritted filter. The resulting wet cake (residue) was dried overnight (about 12–20 hours) using an oven maintained at about 120° C. and subatmospheric pressure.

The resulting dried cake was ground to a fine powder using a mortar and pestle, followed by blending with a sufficient amount of polyphenylene oxide powder on a jar mill to form a pulverulent composite containing 80% powdered dried cake and 20% polyphenylene oxide. The pulverulent composite was compression shaped using a conventional press to form cylindrical tablets of about 1/16 inch in length and about 3/16 inch in diameter.

Catalyst and Process Testing

The reactor—after charging with catalyst pellets—was capped and immersed in the salt bath at 370° C. The catalyst was pre-heated by passing nitrogen through the bath-heated catalyst bed at a volumetric rate corresponding to 2 SCFH (standard cubic feet per hour) for 15 minutes.

Immediately following, under continuous process reaction conditions, liquid feedstock which contained methanol, phenol, ortho-cresol and water, was continuously fed at a rate of 228 ml/hour throughout a 311-hour test. The resulting feed vapors were continuously passed through the catalyst as described above. The conditions and results of the test are set forth in Table V.

TABLE V

| Feed Composition | | | |
|---|---|---|---|
| Molar Ratio Methanol to Phenolic Compounds | 4:1 | | |
| Molar Ratio Phenol to Ortho-Cresol | 60:40 | | |
| Wt. % Water in Feed | 23 | | |
| Operating Conditions | | | |
| Temperature (°C.) | 440–453 | | |
| LHSV (hr.$^{-1}$)[1] | 2.07 | | |
| Pressure (psig) | 0 | | |
| Phenolic Distribution (wt. %) | 195 HR[2] | 311 HR[3] | TWA[4] |
| o-cresol | 19.95 | 16.90 | 21.92 |
| 2,6-xylenol | 70.08 | 73.18 | 65.77 |
| 2,4,6-mesitol | 4.89 | 4.56 | 6.05 |
| Phenol | 4.74 | 5.31 | 6.28 |
| Off Gas | 0.550 | 0.580 | 0.476 |

[1]LHSV is the liquid hourly space velocity and defines the volume of liquid per volume of catalyst per hour.
[2]Temperature at the indicated elapsed time was 453° C.
[3]Temperature at the indicated elapsed time was 453° C.
[4]Time-weighted average of numerous values obtained, at generally uniform intervals throughout the 311-hour test.

The essence of a preferred embodiment of the process of this invention is based on the unexpected efficacy of a catalyst composite containing a major portion of magnesium in the form of magnesium carbonate and a minor proportion of a manganese compound wherein the combination of catalyst components are substantially free of deleterious water-soluble cations or anions, and further wherein the catalyst composites are formed in situ into active ortho-alkylation catalyst species during the ortho-alkylation of phenolic compounds with alcohols.

Further, the efficacy of the process of this invention is optionally acquired without deleterious process side-effects wherein the catalyst composites employed in the process are preformed by wet- or dry-pelleting shaping procedures.

While the invention is described with respect to a particularly preferred embodiment it will be apparent to those of ordinary skill in the art that certain modifications and changes may be made without departing from the spirit instilled in the invention and therefore it is intended that the foregoing disclosure be limited only by the claims appended hereto.

What is claimed is:

1. A catalytic ortho-alkylation process which comprises reacting a phenolic compound of the formula:

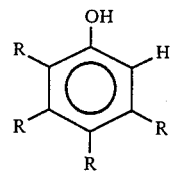

where each R is a monovalent substituent selected from the group consisting of hydrogen, alkyl, phenyl and alkyl-substituted phenyl with an alcohol selected from the group consisting of $C_{1-6}$ alkyl alcohols at a temperature from about 300° C. to the decomposition temperature of the reactants or catalyst in the presence of a catalyst composite consisting essentially of a calcination residue derived at said reaction temperatures from an admixture of magnesium carbonate and/or magnesium hydroxide and a manganese compound wherein said admixture is formed by precipitating said manganese compound in the presence of magnesium carbonate and/or magnesium hydroxide.

2. The claim 1 process wherein the catalyst is formed from an admixture of manganese hydroxide co-precipitated with magnesium carbonate from an aqueous slurry.

3. The claim 2 process wherein the magnesium carbonate is basic magnesium carbonate.

4. The claim 3 process wherein the basic magnesium carbonate has the formula $xMgCO_3 \cdot Mg(OH)_2 \cdot xH_2O$ wherein independently each x is a number average of from about 3 to about 5.

5. The claim 1 process wherein the catalyst is formed from an admixture of manganese hydroxide co-precipitated with magnesium hydroxide from an aqueous slurry.

6. The claim 1 process wherein the catalyst is formed from an admixture of magnesium carbonate, magnesium hydroxide, and manganese hydroxide co-precipitated from an aqueous slurry.

7. The claim 1 process wherein the reaction pressure is between about 0.5 and about 5 atmospheres.

8. The claim 1 process wherein the reaction temperature is between about 350° C. to 500° C.

9. A catalytic ortho-alkylation process which comprises reacting a mixture containing phenol and ortho-cresol with methanol at a temperature of from 350° C.

to 500° C. in the presence of a catalyst composite consisting essentially of a calcination residue derived from heating at a temperature of at least 300° C. in an inert nitrogen atmosphere an admixture of manganese hydroxide coprecipitated with basic magnesium carbonate having the formula $xMgCO_3 \cdot Mg(OH)_2 \cdot xH_2O$ wherein independently each x is a number average of from about 3 to about 5, from an aqueous slurry, wherein the catalyst before heating contains up to about 20 weight percent of a polyphenylene oxide resin.

10. The claim 9 process wherein the reaction is carried out in the presence of water.

11. The claim 10 process wherein the catalyst precursor is substantially free of deleterious water-soluble cations or anions.

12. The claim 9 process wherein the reaction pressure is between about 0.5 and about 5 atmospheres.

13. The claim 9 process wherein the reaction products comprise at least about 65 percent 2,6-xylenol, and less than about 4 percent 2,4,6-mesitol by weight.

14. The claim 9 process wherein the reaction products comprise at least 70 percent 2,6-xylenol, and less than about 4 percent 2,4,6-mesitol by weight.

15. The claim 1 process wherein the admixture contains up to 20 percent by weight of a polyphenylene oxide resin before heating.

16. The claim 1 process wherein the catalyst is formed from an admixture of magnesium carbonate, magnesium hydroxide, and manganese hydroxide coprecipitated from an aqueous slurry.

17. The claim 1 process wherein the admixture contains a water-soluble synthetic resin shaping aid.

* * * * *

UNITED STATES PATENT AND TRADEMARK OFFICE
CERTIFICATE OF CORRECTION

PATENT NO. : 4,528,407
DATED : July 9, 1985
INVENTOR(S) : William E. Smith & Richard A. Battista It is certified that error appears in the above—identified patent and that said Letters Patent is hereby corrected as shown below:

In column 12, on line 12, change "1" to --9--.

Signed and Sealed this

Eleventh Day of March 1986

[SEAL]

Attest:

DONALD J. QUIGG

Attesting Officer

Commissioner of Patents and Trademarks